United States Patent
Hagiwara et al.

(10) Patent No.: US 11,147,656 B2
(45) Date of Patent: Oct. 19, 2021

(54) METHOD FOR PRODUCING ARTIFICIAL TEETH

(71) Applicant: DWS SRL, Zane' (IT)

(72) Inventors: Tsuneo Hagiwara, Tokyo (JP); Satoshi Iketani, Vicenza (IT)

(73) Assignee: DWS S.R.L, Zane' (IT)

( * ) Notice: Subject to any disclaimer, the term of this patent is extended or adjusted under 35 U.S.C. 154(b) by 218 days.

(21) Appl. No.: 14/908,215

(22) PCT Filed: Jul. 16, 2014

(86) PCT No.: PCT/IB2014/001334
§ 371 (c)(1),
(2) Date: Mar. 11, 2016

(87) PCT Pub. No.: WO2015/028855
PCT Pub. Date: Mar. 5, 2015

(65) Prior Publication Data
US 2016/0184189 A1    Jun. 30, 2016

(30) Foreign Application Priority Data

Aug. 27, 2013    (JP) .............................. JP2013-175277

(51) Int. Cl.
*A61C 13/087*    (2006.01)
*B29C 64/135*    (2017.01)
(Continued)

(52) U.S. Cl.
CPC ............ *A61C 13/087* (2013.01); *A61C 13/20* (2013.01); *A61K 6/887* (2020.01); *B29C 35/041* (2013.01);
(Continued)

(58) Field of Classification Search
CPC ........ A61K 6/083; B33Y 70/00; B33Y 80/00; B33Y 50/02; B33Y 10/00; B29C 64/135;
(Continued)

(56) References Cited

U.S. PATENT DOCUMENTS 4,725,631 A * 2/1988 Bastioli .................. C08F 20/30
                                                            523/115
5,147,903 A * 9/1992 Podszun .............. A61K 6/0017
                                                            523/115
(Continued)

FOREIGN PATENT DOCUMENTS

CA        2371357 A1    9/2002
CN        103642382 A    3/2014
(Continued)

OTHER PUBLICATIONS

Robert G. Craig et al. (2006). "Dental Materials". Ullmann's Encyclopedia of Industrial Chemistry. Weinheim: Wiley;<doi: 10.1002/14356007.a08_251.pub2> (Year: 2012).*

(Continued)

*Primary Examiner* — Leith S Shafi
(74) *Attorney, Agent, or Firm* — Volpe Koenig

(57) ABSTRACT

To provide a method for producing an artificial tooth which is excellent in strength, abrasion resistance, hardness, low water absorption, aesthetic property, functionality, and the like within a short time, especially less than 1 hour, smoothly and simply, without requiring skill using a dental photocurable resin composition.
[Solution]
Disclosed is a method for producing an artificial tooth, which includes the steps of:
(a) accommodating a liquid dental photocurable resin composition containing a radical polymerizable organic com-
(Continued)

pound (A), a filler (B), and a photosensitive radical polymerization initiator (C) in a shaping container having a light permeable bottom face, and irradiating the dental photocurable resin composition in the shaping container with light in a predetermined shape pattern through the light permeable bottom face of the shaping container in accordance with slice data every one layer based on three-dimensional CAD data relating to a tooth to form a cured resin layer having a shape pattern for one layer;

(b) lifting up the cured resin layer for one layer formed in the step (a), thereby allowing the liquid dental photocurable resin composition to flow into the space between the lower face of the cured resin layer and the bottom face of the shaping container, and irradiating the dental photocurable resin composition between the lower face of the cured resin layer and the bottom face of the shaping container with light through the light permeable bottom face of the shaping container in accordance with slice data every one layer based on three-dimensional CAD data relating to a tooth to further form a cured resin layer having a shape pattern for one layer; and (c) repeating the operation of the step (b) until the objective artificial tooth is obtained.

9 Claims, 2 Drawing Sheets

(51) Int. Cl.

| | | |
|---|---|---|
| *A61C 13/20* | (2006.01) | |
| *B33Y 70/00* | (2020.01) | |
| *A61K 6/887* | (2020.01) | |
| *B29C 64/386* | (2017.01) | |
| *B29C 35/04* | (2006.01) | |
| *B29C 35/08* | (2006.01) | |
| *B33Y 80/00* | (2015.01) | |
| *B33Y 10/00* | (2015.01) | |
| *B33Y 50/02* | (2015.01) | |
| *B29K 63/00* | (2006.01) | |
| *B29K 75/00* | (2006.01) | |
| *B29K 105/16* | (2006.01) | |
| *B29K 105/24* | (2006.01) | |
| *B29L 31/00* | (2006.01) | |

(52) U.S. Cl.
CPC ........ *B29C 35/0805* (2013.01); *B29C 64/135* (2017.08); *B29C 64/386* (2017.08); *B33Y 70/00* (2014.12); *B29C 2035/0827* (2013.01); *B29K 2063/00* (2013.01); *B29K 2075/00* (2013.01); *B29K 2105/16* (2013.01); *B29K 2105/24* (2013.01); *B29K 2995/007* (2013.01); *B29K 2995/0069* (2013.01); *B29K 2995/0077* (2013.01); *B29K 2995/0082* (2013.01); *B29K 2995/0087* (2013.01); *B29L 2031/7536* (2013.01); *B33Y 10/00* (2014.12); *B33Y 50/02* (2014.12); *B33Y 80/00* (2014.12)

(58) Field of Classification Search
CPC .............. B29C 35/041; B29C 35/0805; B29C 2035/0827; B29C 64/106; B29C 64/124; B29C 64/129; A61C 13/20; A61C 13/087; B29K 2995/0069; B29K 2075/00; B29K 2105/24; B29K 2995/0087; B29K 2995/007; B29K 2995/0077; B29K 2995/0082; B29K 2063/00; B29K 2105/16; B29L 2031/7536
See application file for complete search history.

(56) References Cited

U.S. PATENT DOCUMENTS

| | | |
|---|---|---|
| 5,886,064 A | 3/1999 | Rheinberger et al. |
| 6,017,973 A * | 1/2000 | Tamura ................. B29C 39/003 522/96 |
| 6,200,732 B1 * | 3/2001 | Tamura ................. G03F 7/0037 430/284.1 |
| 6,203,966 B1 * | 3/2001 | Tamura ................. C08K 3/22 430/284.1 |
| 6,413,698 B1 | 7/2002 | Tamura et al. |
| 7,141,616 B2 * | 11/2006 | Hecht ................... A61K 6/893 523/115 |
| 2002/0012754 A1 | 1/2002 | Yamamura et al. |
| 2006/0052470 A1* | 3/2006 | Grech ................... A61K 6/083 522/6 |
| 2009/0220916 A1* | 9/2009 | Fisker ................... A61C 9/00 433/201.1 |
| 2010/0029801 A1* | 2/2010 | Moszner .............. A61K 6/0215 522/167 |
| 2011/0310370 A1 | 12/2011 | Rohner et al. |
| 2012/0021383 A1 | 1/2012 | Skaria et al. |
| 2013/0295212 A1* | 11/2013 | Chen ..................... B29C 64/129 425/150 |
| 2016/0184189 A1 | 6/2016 | Hagiwara et al. |

FOREIGN PATENT DOCUMENTS

| | | |
|---|---|---|
| DE | 101 14 290 B4 | 8/2004 |
| DE | 10 2007 010 624 A1 | 9/2008 |
| EP | 0 346 707 A2 | 12/1989 |
| EP | 0 346 707 A3 | 12/1989 |
| EP | 0348061 B1 | 10/1995 |
| EP | 0802455 A1 | 10/1997 |
| EP | 3040046 A1 | 7/2016 |
| GB | 1352063 A | 5/1974 |
| GB | 1465897 A | 3/1977 |
| GB | 1498421 A | 1/1978 |
| JP | 4-52042 | 12/1992 |
| JP | 5-194135 | 8/1993 |
| JP | 3419488 | 4/2003 |
| JP | 2011-85614 | 4/2011 |
| WO | WO 2005/051332 A1 | 6/2005 |
| WO | 2010045950 A1 | 4/2010 |
| WO | 2011087832 A1 | 7/2011 |
| WO | 2014078537 A1 | 5/2014 |
| WO | 2015028855 A1 | 3/2015 |

OTHER PUBLICATIONS

McClurkin, Joel E., and David W. Rosen. "Computer-aided build style decision support for stereolithography." Rapid Prototyping Journal (1998). (Year: 1998).*

English language translation of Publication No. JP,H04-52042, Y2.

English language translation of JPH05194135 (A).

English language translation of Bibliographic data of JP3419488 (B2)—Also published as JPH06256131 (A).

English language translation of JP2011085614 (A).

Kawaguchi et al., Effect of Aliphatic Dimethacrylate Diluent on the Properties of UDMA Resin Systems, The Japanese Society for Dental Materials and Devices, vol. 7, No. 5 715-719 (1988).

English language translation of Kawaguchi et al., Effect of Aliphatic Dimethacrylate on the Physical Properties of UDMA-Based Resins The Japanese Society for Dental Materials and Devices, Dental Materials and Instruments vol. 7, No. 5715-719 (1988).

Mikito Deguchi, Artificial teeth used for dentures (Overview)—Key Words: Basic technology of synthetic polymer teeth for dentures (2013).

English language translation of Mikito Deguchi, Artificial Teeth Used for Dentures (Prosthetic Dental Implants) (Overview)—Manufacturing and and Technology, vol. 65, No. 3 (2013).

PCT International Search Report, dated Nov. 13, 2014, corresponding to International Application No. PCT/IB2014/001334.

(56) References Cited

OTHER PUBLICATIONS

PCT Written Opinion of the International Search Authority, dated Nov. 13, 2014, corresponding to International Application No. PCT/IB2014/001334.
English language translation of EP Application No. EP0346707.
Quintessenz Zahntech 2009; 35(9): 1144-1153.
User Instructions Deltamed e-dent 100, Jan. 7, 2010.
Safety Data Sheet Deltamed e-dent 100, Dec. 10, 2009.
Preliminary Opposition filed against European patent 3040046; Sep. 17, 2019.

* cited by examiner

METHOD FOR PRODUCING ARTIFICIAL TEETH

TECHNICAL FIELD

The present invention relates to a method for producing an artificial tooth, and a photocurable resin composition for an artificial tooth used therefor. More specifically, the present invention relates to a method for producing an artificial tooth, which is excellent in aesthetic property, hardness, strength, functionality, fitness, and the like in a short time, simply and smoothly, and a photocurable resin composition for an artificial tooth used therefor.

BACKGROUND ART

In place of a natural tooth lost by dental caries (decayed tooth), external injury, periodontal disease, and the like, an artificial tooth such as a false tooth or denture has widely been used so as to recover a function thereof. Examples of the artificial tooth include porcelain tooth, resin tooth, metal tooth, composite tooth made of porcelain and metal, composite tooth made of resin and metal, and the like.

Of the artificial teeth mentioned above, a porcelain tooth is excellent in durability, stain resistance, hardness, mechanical strength, aesthetic property, functionality, and the like, and is used as a true tooth. The porcelain tooth is produced by grinding a ceramic material such as zirconia, one by one, using a computerized numerically controlled machine (CNC device), thus requiring labor and time for the production, leading to higher price.

Meanwhile, the resin tooth includes a resin tooth as a provisional tooth used only for a short time until a final tooth is mounted, and a resin tooth used as a true tooth.

It is necessary for the provisional tooth (resin tooth for a provisional tooth) to be mounted in the oral cavity immediately after performing a treatment such as tooth grinding or tooth extraction since it is an artificial tooth mounted temporarily so as not to cause inconvenience in eating and drinking, and other daily life until the final tooth is completed.

The method for producing a provisional tooth which has widely been used heretofore includes the following method. That is, after mold making, gypsum is poured into the mold to obtain a model, which is attached to an articulator on this model. After fixing with a frame of metal, a spring, or the like on the model, artificial teeth are arranged on gingival of wax where a tooth is absent. In this state, the artificial tooth is mounted into the oral cavity of the patient, checked up, and then confirmed in alignment and deformation to be completed. A method is also exemplified in which, after mold making, a silicone mold is produced and a curable resin is injected into the silicone mold, followed by curing to produce a provisional tooth. This method has an advantage that a provisional tooth fitted to the patient can be produced, but requires labor and time for the production, several hours or more in some cases. Therefore, it is necessary for the patient to wait for a long time until the provisional tooth is mounted.

Another method for producing a provisional tooth includes a method in which plural provisional teeth made of a resin are stored in a dental clinic in advance, and provisional teeth suited for the patient are selected therefrom, and then a dentist per se or dental technician performs partially grinding so as to fit to the patient. In the case of employing this method, a provisional tooth can be produced in a comparatively short time, but depends largely on the degree of proficiency level of skill of a dentist or a dental technician. If the dentist or dental technician has insufficient skill, it is not easy to obtain a provisional tooth fitted to the patient.

There is also known a method in which a provisional tooth for individual patient is produced by a dentist per se or a dental technician grinding resin lump. In the case of employing this method, when a dentist or a dental technician has a skill and also the number of the provisional tooth to be produced is small such as one, it is possible to produce a provisional tooth fitted to the patient in a comparatively short time. However, when a dentist or a dental technician has insufficient skill, there arises a problem that a long time is required to produce only one provisional tooth, and thus the produced provisional tooth does not fit to the patient. Moreover, when the number of the provisional tooth is large, a long time is required to produce the provisional tooth even in the case of a skilled dentist or dental technician.

A curable resin composition mainly composed of a radical polymerizable organic compound has been made practical for filling or repairing of dental caries (decayed tooth), fracture, and the like of a natural tooth, for bonding of an artificial dental crown and a natural tooth, for an artificial tooth crown, for an artificial tooth, or denture base. In particular, a dental photocurable resin composition, which is referred to as a composite, including a radical polymerizable organic compound as a resin matrix, and a filler and a photosensitive radical polymerization initiator has been widely used since it is curable by short-term light irradiation and has satisfactory operability (see Patent documents 1 and 2). In that case, there has widely been used, as a composite resin for filling, a rigid resin for dental crown, and a base component for an artificial tooth, radical polymerizable organic compounds such as urethane-based dimethacrylate, 2,2-bis[4-(3-(meth)acryloyloxy)-2-hydroxypropoxyphenyl] propane (Non-Patent documents 1 and 2).

Meanwhile, there has been proposed a method for optical stereoscopic shaping of a tooth model, which is used when a dental student performs training of a root canal treatment of a tooth, by repeating a laminating operation of selectively irradiating a surface of a photocurable liquid composition accommodated in a shaping container from above to sequentially form a cured resin layer (Patent document 3).

Furthermore, there has been proposed a method in which a dental impression model is produced based on three-dimensional dental impression data obtained from a computed tomography device (CT device), a magnetic resonance imaging device (MRI), a computed radiographic device (CR device), and the like (Patent documents 4 and 5).

Recently, intraoral tooth-shaped three-dimensional data of the patient are obtained using an intraoral scanner, thus enabling a dental treatment and production of an artificial tooth based on three-dimensional data obtained thereby.

However, the present inventors made an attempt to produce an artificial tooth by the method disclosed in Patent documents 3 to 5, especially stereolithography disclosed in Patent document 3 in which lamination shaping is performed by irradiating a surface of a photocurable resin composition accommodated in a shaping container with light from above, using a dental photocurable resin composition containing a radical polymerizable organic compound, a filler, and a photosensitive radical polymerization initiator, which is used widely in the production of an artificial tooth. However, the dental photocurable resin composition did not undergo sufficient photocuring, thus failing to smoothly produce an artificial tooth which is excellent in hardness, mechanical properties, aesthetic property, and the like in a short time of less than 1 hour.

PRIOR ART DOCUMENTS

Patent Documents

[Patent document 1] JP 3419488 B1
[Patent document 2] JP H5-194135 A
[Patent document 3] JP 2011-85614 A
[Patent document 4] US 2008/0,306,709 A
[Patent document 5] US 2009/0,220,916 A
[Patent document 6] JP 4-52042 Y
[Patent document 7] US 2002/0,155,189 A Non-Patent Documents

[Non-Patent document 1] "Dental Material/Apparatus (Shika Zairyo/Kikai)", 1988, Vol. 7, No. 5, p. 715-718
[Non-Patent document 2] "Production and Technology (Seisan to Gijutsu)", 2013, Vol. 65, No. 3, p. 54-59.

DISCLOSURE OF THE INVENTION

Problems to be Solved by the Invention

An object of the present invention is to provide a method capable of producing an artificial tooth which has various properties required to the artificial tooth, such as strength, abrasion resistance, hardness, and low water absorption, and also has excellent aesthetic property and functionality in a short time, especially in a short time of less than 1 hour, smoothly and simply, using a dental photocurable resin composition containing a radical polymerizable organic compound, a filler, and a photosensitive radical polymerization initiator. Another object of the present invention is to provide a method capable of simply producing an artificial tooth which has various properties required to the artificial tooth, such as strength, abrasion resistance, hardness, and low water absorption, and is also excellent in aesthetic property and functionality in a short time using the above-mentioned dental photocurable resin composition, without being influenced by the degree of proficiency level of skill of a dentist or a dental technician.

Still another object of the present invention is to provide a dental photocurable resin composition for use in the above-mentioned method.

Means for Solving the Problems

The present inventors have intensively studied so as to achieve the above objects. As a result, they have found that, in the production of an artificial tooth with stereolithography using a liquid dental photocurable resin composition containing a radical polymerizable organic compound, a filler, and a photosensitive radical polymerization initiator, when employing a method including the steps of using, as a shaping container for accommodating a dental photocurable resin composition, a shaping container having a light permeable bottom face, and accommodating a dental photocurable resin composition in the shaping container; irradiating with light in a predetermined shape pattern through the light permeable bottom face of the shaping container in accordance with slice data every one layer based on three-dimensional CAD data relating to a tooth to form a cured resin layer; lifting up the cured resin layer for one layer, thereby allowing the liquid dental photocurable resin composition to flow into the space formed between the lower face of the cured resin layer and the bottom face of the shaping container; and repeating a laminating operation of irradiating the dental photocurable resin composition between the lower face of the cured resin layer and the bottom face of the shaping container with light in a predetermined shape pattern through the light permeable bottom face of the shaping container in accordance with slice data every one layer based on three-dimensional CAD data relating to a tooth to form a cured resin layer having a shape pattern for one layer, it is possible to simply produce the objective artificial tooth in a significantly shorter time than usual, for example, in an optical shaping time of usually less than 30 minutes when one artificial tooth is produced, or in an optical shaping time of less than 40 minutes when three artificial teeth are produced.

It has also been found that, according to the method, it is possible to simply produce an artificial tooth which has various properties required to the artificial tooth, such as strength, abrasion resistance, hardness, and low water absorption, and is also excellent in aesthetic property and functionality without being influenced by the degree of proficiency level of skill. Thus, the present invention has been completed based on these findings.

Thus, the present invention is directed to:
(1) A method for producing an artificial tooth, which includes the steps of:
(a) accommodating a liquid dental photocurable resin composition containing a radical polymerizable organic compound (A), a filler (B), and a photosensitive radical polymerization initiator (C) in a shaping container having a light permeable bottom face, and irradiating the dental photocurable resin composition in the shaping container with light in a predetermined shape pattern through the light permeable bottom face of the shaping container in accordance with slice data every one layer based on three-dimensional CAD data relating to a tooth to form a cured resin layer having a shape pattern for one layer;
(b) lifting up the cured resin layer for one layer formed in the step (a), thereby allowing the liquid dental photocurable resin composition to flow into the space between the lower face of the cured resin layer and the bottom face of the shaping container, and irradiating the dental photocurable resin composition between the lower face of the cured resin layer and the bottom face of the shaping container with light in a predetermined shape pattern through the light permeable bottom face of the shaping container in accordance with slice data every one layer based on three-dimensional CAD data relating to a tooth to further form a cured resin layer having a shape pattern for one layer, and
(c) repeating the operation of the step (b) until the objective artificial tooth is obtained.

The present invention is also directed to:
(2) The method for producing an artificial tooth according to the above (1), wherein three-dimensional CAD data relating to a tooth are data obtained using a computed tomography device (CT device), a magnetic resonance imaging device (MRI), a computed radiographic device (CR device), or an intraoral 3D scanner.

The present invention is also directed to:
(3) The method for producing an artificial tooth according to the above (1) or (2), wherein, in the liquid dental photocurable resin composition, the content of the radical polymerizable organic compound (A) is 30 to 95% by mass based on the total mass of the dental photocurable resin composition, the content of filler (B) is 5 to 70% by mass based on the total mass of the dental photocurable resin composition, and the content of the photosensitive radical polymerization initiator (C) is 0.01 to 5% by mass based on the mass of the based on the mass of the radical polymerizable organic compound (A).

Furthermore, the present invention is directed to:

(5) The method for producing an artificial tooth according to any one of the above (1) to (3), wherein the liquid dental photocurable resin composition contains, as at least a portion of the radical polymerizable organic compound (A), at least one of a urethane-based di(meth)acrylate compound (A-1a) obtained by the reaction of 1 mol of an organic diisocyanate compound with 2 mol of hydroxyalkyl (meth) acrylate, represented by the following general formula (A-1a):

$$D\text{-}\{NH\text{---}CO\text{---}O\text{---}R^2\text{---}O\text{---}CO\text{---}C(R^1)\text{=}CH_2\}_2 \qquad (A\text{-}1a)$$

wherein $R^1$ represents a hydrogen atom or a methyl group, $R^2$ represents an alkylene group, and D represents an organic diisocyanate compound residue, and a di(meth)acrylate compound (A-1b) obtained by the reaction of 1 mol of a diepoxy compound with 2 mol of (meth)acrylic acid, represented by the following general formula (A-1b):

$$E\text{-}\{C(H)(OH)\text{---}CH_2\text{---}O\text{---}CO\text{---}C(R^3)\text{=}CH_2\}_2 \qquad (A\text{-}1b)$$

wherein $R^3$ represents a hydrogen atom or a methyl group, and E represents a diepoxy compound residue; and (5) The method for producing an artificial tooth according to the above (4), wherein the content of at least one of the urethane-based di(meth)acrylate compound (A-1a) and the di(meth)acrylate compound (A-1b) is 5 to 95% by mass based on the mass of the radical polymerizable organic compound (A).

The present invention is also directed to:

(6) The method for producing an artificial tooth according to the above (4) or (5), wherein the liquid dental photocurable resin composition contains, as the radical polymerizable organic compound (A), the other radical polymerizable organic compound (A-2), together with at least one of the urethane-based di(meth)acrylate compound (A-1a) and the di(meth)acrylate compound (A-1b);

(7) The method for producing an artificial tooth according to claim 6, wherein the content of the other radical polymerizable organic compound (A-2) is 5 to 70% by mass based on the mass of the radical polymerizable organic compound (A); and (8) The method for producing an artificial tooth according to the above (6) or (7), wherein the liquid dental photocurable resin composition contains, as the other radical polymerizable organic compound (A-2), at least one di(meth)acrylate compound (A-2a) obtained by the ester reaction of 1 mol of the organic diol compound with 2 mol of (meth)acrylic acid, represented by the following general formula (A-2a):

$$G\text{-}\{O\text{---}CO\text{---}C(R^4)\text{=}CH_2\}_2 \qquad (A\text{-}2a)$$

wherein $R^4$ represents a hydrogen atom or a methyl group, and G represents an organic diol compound residue.

The present invention is directed to:

(9) The method for producing an artificial tooth according to any one of the above (1) to (8), wherein the liquid dental photocurable resin composition contains, as the filler (B), at least one of a silica powder, an alumina powder, a zirconia powder, a glass powder, and powders prepared by treating the above powders with a coupling agent; and

(10) The method for producing an artificial tooth according to any one of the above (1) to (9), wherein a liquid dental photocurable resin composition is irradiated with light converted to a spot shape using a line drawing system of linearly moving through the light permeable bottom face of the shaping container to form a cured resin layer, or a liquid dental photocurable resin composition is planarly irradiated with light passed through a planar drawing mask formed by arranging a plurality of micro-optical shutters through the light permeable bottom face of the shaping container.

Furthermore, the present invention is directed to:

(11) A liquid dental photocurable resin composition including a radical polymerizable organic compound (A), a filler (B), and a photosensitive radical polymerization initiator (C) for use in the method for producing an artificial tooth according to any one of the above (1) to (10);

(12) The liquid dental photocurable resin composition according to the above (11), which contains, as at least a portion of the radical polymerizable organic compound (A), at least one of a urethane-based di(meth)acrylate compound (A-1a) obtained by the reaction of 1 mol of an organic diisocyanate compound with 2 mol of hydroxyalkyl (meth) acrylate, represented by the following general formula (A-1a):

$$D\text{-}\{NH\text{---}CO\text{---}O\text{---}R^2\text{---}O\text{---}CO\text{---}C(R^1)\text{=}CH_2\}_2 \qquad (A\text{-}1a)$$

wherein $R^1$ represents a hydrogen atom or a methyl group, $R^2$ represents an alkylene group, and D represents an organic diisocyanate compound residue, and a di(meth)acrylate compound (A-1b) obtained by the reaction of 1 mol of a diepoxy compound with 2 mol of (meth)acrylic acid, represented by the following general formula (A-1b):

$$E\text{-}\{C(H)(OH)\text{---}CH_2\text{---}O\text{---}CO\text{---}C(R^3)\text{=}CH_2\}_2 \qquad (A\text{-}1b)$$

wherein $R^3$ represents a hydrogen atom or a methyl group, and E represents a diepoxy compound residue; and

(13) The liquid dental photocurable resin composition according to the above (11) or (12), wherein every radical polymerizable organic compound (A) is a methacrylate-based compound.

Effects of the Invention

According to the present invention, it is possible to produce an artificial tooth which has various properties required to the artificial tooth, such as strength, abrasion resistance, hardness, and low water absorption, and is also excellent in aesthetic property and functionality in a short time, especially in a short time of less than 1 hour, smoothly and simply, using a liquid dental photocurable resin composition containing a radical polymerizable organic compound, a filler, and a photosensitive radical polymerization initiator.

According to the present invention, it is possible to simply produce an artificial tooth which has various properties required to the artificial tooth, such as strength, abrasion resistance, hardness, and low water absorption, and is also excellent in aesthetic property and functionality in a short time using the above-mentioned dental photocurable resin composition, without being influenced by the degree of proficiency level of skill of a dentist or a dental technician. Furthermore, according to the present invention, it is possible to smoothly produce an artificial tooth which is excellent in aesthetic property, hardness, strength, functionality, and fitness in a significantly short time even when using an inexpensive light source capable of emitting light having a wavelength of 380 to 450 nm (light in a visible range) without using an expensive light source capable or emitting ultraviolet laser beam having a wavelength of 300 to 370 nm which has usually been used when a stereoscopically shaped article is produced by emitting light from the upper surface of a photocurable resin composition. Thus, the present invention is also excellent in view of handiness, economy, maintainability of an optical shaping device, and the like.

MODE FOR CARRYING OUT THE INVENTION

Figure 1:
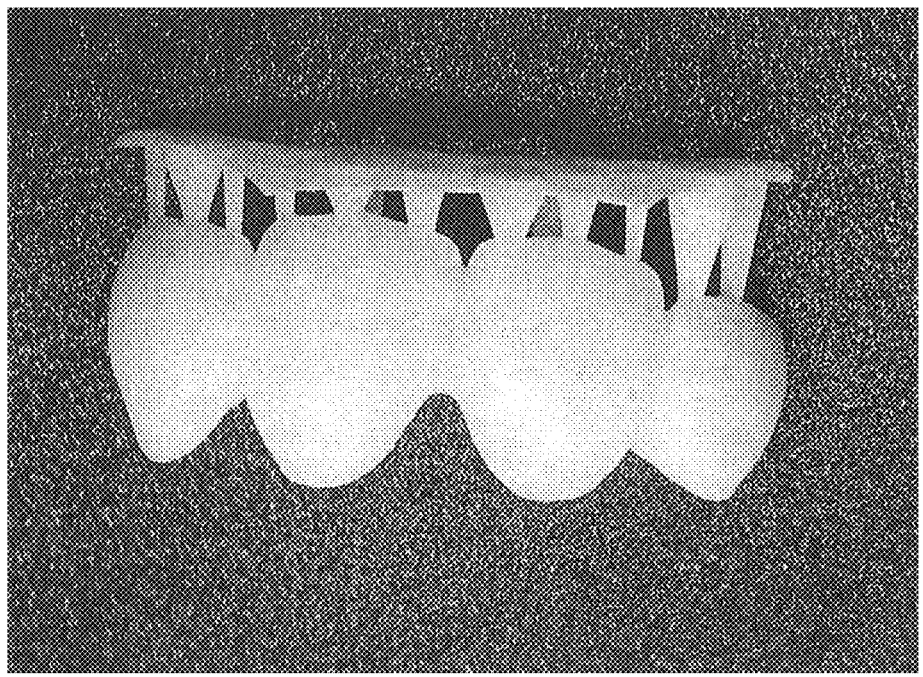
FIG. 1 is a photograph taking a provisional tooth before cutting off a supporting member obtained in Example 1 (provisional tooth including a supporting member).

The present invention will be described in detail below.

In the present invention, a liquid dental photocurable resin composition containing a radical polymerizable organic compound (A), a filler (B), and a photosensitive radical polymerization initiator (C) is used as the material for the production of an artificial tooth.

It is possible to use, as the radical polymerizable organic compound (A) in the dental photocurable resin composition, any radical polymerizable organic compound as long as it is usable as a dental material. In view of availability and reactivity, a (meth)acrylic compound having one, or two or more acrylic group(s) and/or methacrylic group(s) in a molecule is preferably used.

Of these compounds, the dental photocurable resin composition used in the present invention preferably contains, as at least a portion of the radical polymerizable organic compound (A), at least one of a urethane-based di(meth)acrylate compound (A-1a) obtained by the reaction of 1 mol of an organic diisocyanate compound with 2 mol of hydroxyalkyl (meth)acrylate, represented by the following general formula (A-1a):

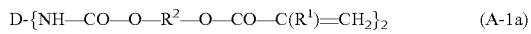
$$D\text{-}\{NH\text{---}CO\text{---}O\text{---}R^2\text{---}O\text{---}CO\text{---}C(R^1)\text{=}CH_2\}_2 \quad (A\text{-}1a)$$

wherein $R^1$ represents a hydrogen atom or a methyl group, $R^2$ represents an alkylene group, and D represents an organic diisocyanate compound residue (group after removing two isocyanate groups from organic diisocyanate compound), and a di(meth)acrylate compound (A-1b) obtained by the reaction of 1 mol of a diepoxy compound with 2 mol of (meth)acrylic acid, represented by the following general formula (A-1b):

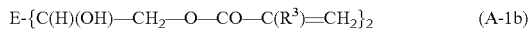
$$E\text{-}\{C(H)(OH)\text{---}CH_2\text{---}O\text{---}CO\text{---}C(R^3)\text{=}CH_2\}_2 \quad (A\text{-}1b)$$

wherein $R^3$ represents a hydrogen atom or a methyl group, and E represents a diepoxy compound residue (group after removing two epoxy groups from diepoxy compound), in view of compatibility with the human body, ease of availability, mechanical properties, and the like.

In the above general formula (A-1a), the organic diisocyanate compound residue D may be any of an aromatic diisocyanate compound residue, an aliphatic diisocyanate compound residue, and an alicyclic diisocyanate compound residue.

Examples of the urethane-based di(meth)acrylate-based compound (A-1a) include, but are not limited to, urethane di(meth)acrylates obtained by the reaction of 1 mol of an organic diisocyanate compound composed of one, or two or more aliphatic diisocyanate compound(s) such as hexamethylene diisocyanate, 2,2,4-trimethylhexamethylene diisocyanate, isophorone diisocyanate, hydrogenated diphenylmethane diisocyanate, hydrogenated m-xylylene diisocyanate, and hydrogenated toluene diisocyanate, and aromatic diisocyanates such as diphenylmethane diisocyanate, toluene diisocyanate, and xylylene diisocyanate with 2 mol of a hydroxyalkyl ester whose (meth)acrylic acid has 2 to 6 carbon atoms, such as hydroxyethyl (meth)acrylate, hydroxypropyl (meth)acrylate, hydroxybutyl (meth)acrylate, hydroxypentyl (meth)acrylate, and hydroxyhexyl (meth)acrylate [(meth)acrylic acid ester obtained by the reaction of 1 mol of an alkylenediol having 2 to 6 carbon atoms with 1 mol of (meth)acrylic acid].

More specific examples thereof include urethane di(meth)acrylate obtained by reacting 1 mol of 2,2,4-trimethylhexamethylene diisocyanate with 2 mol of hydroxyethyl (meth)acrylate, urethane di(meth)acrylate obtained by reacting 1 mol of isophorone diisocyanate with 2 mol of hydroxyethyl (meth)acrylate, urethane di(meth)acrylate obtained by reacting 1 mol of hydrogenated diphenylmethane diisocyanate with 2 mol of hydroxyethyl (meth)acrylate, urethane di(meth)acrylate obtained by reacting 1 mol of 2,2,4-trimethylhexamethylene diisocyanate with 2 mol of hydroxypropyl (meth)acrylate, urethane di(meth)acrylate obtained by reacting 1 mol of isophorone diisocyanate with 2 mol of hydroxypropyl (meth)acrylate, urethane di(meth)acrylate obtained by reacting 1 mol of 2,2,4-trimethylhexamethylene diisocyanate with 2 mol of hydroxyethyl (meth)acrylate, urethane di(meth)acrylate obtained by reacting 1 mol of diphenylmethane diisocyanate with 2 mol of hydroxyethyl (meth)acrylate, urethane di(meth)acrylate obtained by reacting 1 mol of diphenylmethane diisocyanate with 2 mol of hydroxypropyl (meth)acrylate, urethane di(meth)acrylate obtained by reacting 1 mol of toluene diisocyanate with 2 mol of hydroxyethyl (meth)acrylate, urethane di(meth)acrylate obtained by reacting 1 mol of toluene diisocyanate with 2 mol of hydroxypropyl (meth)acrylate, and the like, and one, or two or more urethane di(meth)acrylate(s) can be used.

Of these compounds, urethane dimethacrylate obtained by reacting 1 mol of 2,2,4-trimethylhexamethylene diisocyanate with 2 mol of hydroxyethyl methacrylate, so-called UDMA, is preferably used as the urethane-based di(meth)acrylate compound (A-1a) in view of availability, mechanical properties, and compatibility with the human body.

In the above general formula (A-1b), the diepoxy compound residue E may be any of an aromatic diepoxy compound residue, an aliphatic diepoxy compound residue, and an alicyclic diepoxy compound residue.

Examples of the di(meth)acrylate compound (A-1b) include a di(meth)acrylate compound obtained by reacting 1 mol of a diepoxy compound composed of one, or two or more aromatic diepoxy compound(s), alicyclic diepoxy compound(s), and aliphatic diepoxy compound(s) with 2 mol of (meth)acrylic acid, and a di(meth)acrylate compound obtained by reacting 1 mol of an aromatic diepoxy compound with 2 mol of (meth)acrylic acid is preferably use in view of availability, mechanical properties, and compatibility with the human body.

Specific examples thereof include a di(meth)acrylate compound obtained by reacting 1 mol of diglycidyl ether of a bisphenol-based compound such as bisphenol A or bisphenol F with 2 mol of (meth)acrylic acid, a di(meth)acrylate compound obtained by reacting 1 mol of diglycidyl ether, which is obtained by reacting an alkylene oxide adduct of a bisphenol-based compound such as bisphenol A or bisphenol F with an epoxydating agent such as epichlorohydrin, with 2 mol of (meth)acrylic acid, a di(meth)acrylate compound obtained by reacting 1 mol of a novolak type diepoxy compound with 2 mol of (meth)acrylic acid, and the like, and one, or two or more di(meth)acrylate compound(s) can be used.

Of these di(meth)acrylate compounds, a dimethacrylate compound obtained by reacting 1 mol of diglycidyl ether, which is obtained by reacting a bisphenol A compound with epichlorohydrin, with 2 mol of methacrylic acid, so-called BisGMA, is preferably used as the epoxy-based di(meth)acrylate compound (A-1b) in view of availability, mechanical properties, and compatibility with the human body.

The liquid dental photocurable resin composition used in the present invention may contain either or both of a urethane-based di(meth)acrylate compound (A-1a) and a di(meth)acrylate compound (A-1b).

The liquid dental photocurable resin composition used in the present invention can optionally contain the other radical polymerizable organic compound (A-2), together with at least one of a urethane-based di(meth)acrylate compound (A-1a) and a di(meth)acrylate compound (A-1b).

It is possible to adjust the viscosity of the dental photocurable resin composition to the value suited for optical shaping by including the other radical polymerizable organic compound (A-2), together with at least one of a urethane-based di(meth)acrylate compound (A-1a) and a di(meth)acrylate compound (A-1b).

It is possible to use, as the other radical polymerizable organic compound (A-2), any radical polymerizable organic compound which has hitherto been used in a resin composition for optical shaping and, typically, a compound having at least one (meth)acrylic group in a molecule is preferably used, and specific examples thereof include a (meth)acrylic acid ester, polyester (meth)acrylate, polyether (meth)acrylate of alcohols, and the like.

Examples of the (meth)acrylic acid ester of alcohols include a (meth)acrylic acid ester obtained by reacting an aromatic group-containing alcohol having at least one hydroxyl group in the molecule, an aliphatic alcohol, an alicyclic alcohol, or an alkylene oxide adduct of certain alcohols mentioned above with (meth)acrylic acid, and one, or two or more thereof can be used.

More specific examples of the other radical polymerizable organic compound (A-2) include 2-ethylhexyl (meth)acrylate, 2-hydroxyethyl (meth)acrylate, 2-hydroxypropyl (meth)acrylate, lauryl (meth)acrylate, stearyl (meth)acrylate, isooctyl (meth)acrylate, tetrahydrofurfuryl (meth)acrylate, isobornyl (meth)acrylate, benzyl (meth)acrylate, 1,4-butanediol di(meth)acrylate, 1,6-hexanediol di(meth)acrylate, diethylene glycol di(meth)acrylate, triethylene glycol di(meth)acrylate, neopentyl glycol di(meth)acrylate, polyethylene glycol di(meth)acrylate, polypropylene glycol di(meth)acrylate, trimethylolpropane tri(meth)acrylate, pentaerythritol tetra(meth)acrylate, dipentaerythritol hexa(meth)acrylate and the other dipentaerythritol poly(meth)acrylate, (meth)acrylate of an alkylene oxide adduct of the polyhydric alcohols mentioned above such as diol, triol, tetraol, or hexanol, ethylene oxide-modified bisphenol A diacrylate, propylene oxide-modified bisphenol A diacrylate, and the like.

Of these compounds, (meth)acrylate having two or more (meth)acrylic groups in a molecule obtained by the reaction of a dihydric alcohol or a tri- or higher polyhydric alcohol with (meth)acrylic acid is preferably used as the other radical polymerizable organic compound (A-2) in view of availability and reactivity, and, particularly, at least one di(meth)acrylate compound (A-2a) represented by the following general formula (A-2a):

$$G\text{-}\{O\text{—}CO\text{—}C(R^4)\text{=}CH_2\}_2 \quad (A\text{-}2a)$$

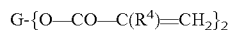

wherein $R^4$ represents a hydrogen atom or a methyl group, G represents an organic diol compound residue (residue after removing two hydroxyl groups from organic diol compound) is preferably used.

In the general formula (A-2a), the organic diol compound residue G may be any of an aromatic diol compound residue, an aliphatic diol compound residue, and an alicyclic diol compound residue, and is preferably an aliphatic diol compound residue in view of availability, viscosity, and reactivity.

Specific examples of the di(meth)acrylate compound (A-2a) include di(meth)acrylates of mono or oligo ethylene glycols, such as diethylene glycol di(meth)acrylate, triethylene glycol di(meth)acrylate, and tetraethylene glycol di(meth)acrylate; di(meth)acrylates of alkylenediols, such as tetramethylene glycol di(meth)acrylate, pentamethylene di(meth)acrylate, and hexamethylene glycol di(meth)acrylate.

Examples of the above-mentioned polyester (meth)acrylate usable as the other radical polymerizable organic compound (A-2) include polyester (meth)acrylate obtained by the reaction of a hydroxyl group-containing polyester with (meth)acrylic acid.

Examples of the above-mentioned polyether (meth)acrylate include polyether (meth)acrylate obtained by the reaction of a hydroxyl group-containing polyether with (meth)acrylic acid.

When the radical polymerizable organic compound (A) is a compound having a (meth)acrylic group, a compound having a methacrylic group is preferable as compared with a compound having an acrylic group in view of biocompatibility.

It is possible to use, as the filler (B) in the dental photocurable resin composition used in the present invention, one, two or more inorganic filler(s) and organic filler(s).

Examples of the inorganic filler include transition metal in Groups I, II, III and IV of The Periodic Table, or oxides, chlorides, sulfites, carbonates, phosphates, silicates thereof, or mixtures thereof.

More specific examples thereof include silicon dioxide (silica) powder, aluminum oxide powder (alumina powder), zirconia powder, glass powders such as lantern glass powder, barium glass powder, and strontium glass powder, quartz powder, barium sulfate powder, titanium oxide powder, glass beads, glass fiber, barium fluoride powder, lead salt powder, glass filler containing talc, silica gel powder, colloidal silica, zirconium oxide powder, tin oxide powder, carbon fiber, and other ceramic powder.

Polymer particles are used as the organic substance filler, and examples thereof include polymethyl methacrylate particles, crosslinked polymethyl methacrylate particles, ethylene-vinyl acetate copolymer particles, styrene-butadiene copolymer particles, acrylonitrile-styrene copolymer particles, ABS resin (acrylonitrile-styrene-butadiene copolymer resin) particles, and the like. The dental photocurable resin composition used in the present invention can contain, as the filler (B), one, or two or more filler(s) mentioned above.

Of the above-mentioned fillers, inorganic fillers are preferably used as the filler (B) in view of an improvement in mechanical properties of a cured article (artificial tooth), and suppression of significant increase in viscosity of the composition. In particular, one, or two or more silica powder(s), alumina powder(s), zirconia powder(s), and glass powder(s) is/are more preferably used in view of mechanical properties and aesthetic property.

It is necessary that the average particle diameter of the filler (B) is smaller than a lamination shaping pitch because of limitation in lamination shaping, and is preferably 0.01 to 50 µm, more preferably 0.01 to 25 µm, still more preferably 0.01 to 10 µm, and particularly preferably 0.1 to 5 µm.

The filler (B) preferably has a spherical shape in view of the fact that the viscosity of the dental photocurable resin composition can be reduced, and more preferably near true sphere.

The filler (B) is preferably surface-treated with a silane coupling agent in view of an improvement in mechanical properties of the artificial tooth. Examples of the silane coupling agent include silane coupling agents having reactive functional group such as a (meth)acrylic group, an epoxy group, a vinyl group, an amino group, and a mercapto group, and one, or two or more filler(s) can be used. Specific examples of the filler treated with a silane coupling agent usable in the present invention include, but are not limited to, a true spherical silica powder and a true spherical alumina powder (Admafine, manufactured by Admatechs Company Limited) treated with methacrylsilane, a spherical glass powder ("Spheriglass", manufactured by Potters Industries Inc.) and zirconia beads (manufactured by NIIMI SANGYO CO., LTD.) treated with methacrylsilane, and the like.

It is possible to use, as the photosensitive radical polymerization initiator (C) in the dental photocurable resin composition used in the present invention, any polymerization initiator capable of initiating radical polymerization of the radical polymerizable organic compound (A) when irradiated with light.

Specific examples of the photosensitive radical polymerization initiator (C) usable in the present invention include, but are not limited to, benzoin ether compounds such as benzoin ethyl ether, benzoin isopropyl ether, and benzoin phenyl ether; acetophenone compounds such as acetophenone, 2,2-dimethoxyacetophenone, and 1,1-dichloroacetophenone; benzyl ketal compounds such as benzyl dimethyl ketal and benzyl diethyl ketal; anthraquinone compounds such as 2-methylanthraquinone, 2-ethylalkylanthraquinone, 2-tertiary-butylanthraquinone, 1-chloroanthraquinone, and 2-amylanthraquinone; phosphine compounds such as triphenylphosphine; benzoylphosphine oxide compounds such as 2,4,6-trimethylbenzoyl-diphenyl-phosphine oxide (Lucirin TPO); bisacylphosphine oxide compounds such as bis(2,4,6-trimethylbenzoyl)-phenylphosphine oxide (Irgacure 819); benzophenone compounds such as benzophenone and 4,4'-bis(N,N'-dimethylamino)benzophenone; thioxanthone and xanthone; acridine derivatives; fexofenadine derivatives; quinoxaline derivatives; 1-phenyl-1,2-propanedion and 2-O-benzoyloxime; 4-(2-hydroxyethoxy)phenyl-(2-propyl)ketone (Irgacure 2959); 1-aminophenyl ketones or 1-hydroxyphenyl ketones, such as 1-hydroxycyclohexyl phenyl ketone, 2-hydroxyisopropyl phenyl ketone, phenyl 1-hydroxyisopropyl ketone, and 4-isopropylphenyl 1-hydroxyisopropyl ketone; and the like.

Of the photosensitive radical polymerization initiators mentioned above, benzoylphosphine oxide such as 2,4,6-trimethylbenzoyl-diphenylphosphine oxide (Lucirin TPO), and bisacylphosphine oxide (Irgacure 819) is preferably used as the photosensitive radical polymerization initiator (C) in view of the fact that the dental photocurable resin composition used in the present invention is capable of satisfactory photocuring under ultraviolet light, near ultraviolet light, and short-wavelength visible light.

In the dental photocurable resin composition used in the present invention, the content of the radical polymerizable organic compound (A) is preferably 30 to 95% by mass based on the total mass of the dental photocurable resin composition. The content of filler (B) is preferably 5 to 70% by mass based on the total mass of the dental photocurable resin composition. The content of the photosensitive radical polymerization initiator (C) is preferably 0.01 to 5% by mass based on the mass of the radical polymerizable organic compound (A). The content of the radical polymerizable organic compound (A) is more preferably 35 to 90% by mass based on the total mass of the dental photocurable resin composition. The content of filler (B) is more preferably 10 to 65% by mass based on the total mass of the dental photocurable resin composition. The content of the photosensitive radical polymerization initiator (C) is more preferably 0.02 to 3% by mass based on the mass of the radical polymerizable organic compound (A).

When the content of the radical polymerizable organic compound (A), the content of the filler (B), and the content of the photosensitive radical polymerization initiator (C) fall within the above range, viscosity and photocuring sensitivity of the dental photocurable resin composition become satisfactory when an artificial tooth is produced, strength, abrasion resistance, hardness, low water absorption, aesthetic property, functionality, and the like of the artificial tooth obtained by optical shaping become satisfactory, and also mechanical properties become satisfactory.

The viscosity of the dental photocurable resin composition is likely to increase when the content of the radical polymerizable organic compound (A) is less than the above-mentioned range, while deterioration of mechanical properties and abrasion resistance of cured article (artificial tooth) is likely to occur when the content is more than the above-mentioned range. Strength, abrasion resistance, hardness, aesthetic property, and the like of the artificial tooth obtained by optical shaping are likely to deteriorate when the content of the filler (B) is less than the above-mentioned range, while the viscosity of the dental photocurable resin composition significantly increases to cause significant deterioration of optical shaping property, leading to deterioration of toughness (durability) of the artificial tooth obtained by optical shaping when the content is more than the above-mentioned range. Sufficient photocuring is less likely to be performed when the content of the photosensitive radical polymerization initiator (C) is less than the above-mentioned range, while mechanical properties of the artificial tooth obtained by optical shaping deteriorate when the content is more than the above-mentioned range.

When the dental photocurable resin composition used in the present invention contains, as the radical polymerizable organic compound (A), at least one of a urethane-based di(meth)acrylate compound (A-1a) and a di(meth)acrylate compound (A-1b), the content (the total content when both compounds are contained) of at least one of the urethane-based di(meth)acrylate compound (A-1a) and the di(meth)acrylate compound (A-1b) is preferably 5 to 95% by mass, more preferably 20 to 80% by mass, and still more preferably 30 to 70% by mass, based on the mass of the radical polymerizable organic compound (A).

When the content of at least one of the urethane-based di(meth)acrylate compound (A-1a) and the di(meth)acrylate compound (A-1b) is within the above range, it is possible to obtain excellent effect of mechanical properties of the artificial tooth obtained by optical shaping.

When the dental photocurable resin composition used in the present invention further contains, as a portion of the radical polymerizable organic compound (A), the other radical polymerizable organic compound (A-2), the content of the other radical polymerizable organic compound (A-2) is preferably 5 to 95% by mass, more preferably 20 to 80% by mass, and still more preferably 30 to 70% by mass, based on the mass of the radical polymerizable organic compound (A).

When the content of the other radical polymerizable organic compound (A-2) is within the above range, it is possible to obtain the effect of an improvement in reactivity, together with the effect of a decrease in viscosity of a photocurable resin composition for an artificial tooth.

In particular, when the other radical polymerizable organic compound (A-2) is a di(meth)acrylate compound (A-2a) represented by the below-mentioned general formula (A-2a), the viscosity of the dental photocurable resin composition becomes the viscosity suited for optical shaping and also high reactivity is obtained by including the di(meth)acrylate compound (A-2a) in the proportion of preferably 10 to 90% by mass, more preferably 20 to 70% by mass, and particularly preferably 30 to 70% by mass, based on the mass of the radical polymerizable organic compound (A).

When the patient wearing the artificial tooth produced by the method of the present invention undergoes a treatment, the dental photocurable resin composition used in the present invention may contain, as the element having X-ray contrast property, an inorganic oxide containing an element having X-ray contrast property (heavy metal element) such as barium, strontium, zirconium, bismuth, tungsten, germanium, molybdenum, and lanthanide so as to enable clear confirmation of the mounted state, shape and state of the artificial tooth by an X-ray photograph.

The dental photocurable resin composition used in the present invention may optionally contain one, or two or more colorant(s) such as pigments and dyes, defoamers, leveling agents, thickeners, flame retardants, antioxidants, curing depth control agents, ultraviolet absorbers, modifier resins, and the like in an appropriate amount as long as the effects of the present invention are not impaired.

In the present invention, the viscosity of the dental photocurable resin composition used in the present invention is preferably 20,000 mPa·s or less, more preferably 15,000 mPa·s or less, and still more preferably 10,000 mPa·s or less, when measured at 25° C. so as to allow the dental photocurable resin composition to smoothly flow into the space between the cured resin layer lifted up only by one layer and the light permeable bottom face of the shaping container at the time of the production of an artificial tooth.

The viscosity of the dental photocurable resin composition can be controlled by selecting kinds and combinations of the radical polymerizable organic compound (A), kinds and average particle diameters of the filler (B), mixing ratios of the radical polymerizable organic compound (A) and the filler (B), and the like.

In the present invention, an artificial tooth is produced by the optical shaping steps of:
(a) accommodating the above liquid dental photocurable resin composition in a shaping container having a light permeable bottom face, and irradiating the dental photocurable resin composition in the shaping container with light in a predetermined shape pattern through the light permeable bottom face of the shaping container in accordance with slice data every one layer based on three-dimensional CAD data relating to a tooth to form a cured resin layer having a predetermined shape pattern for one layer;
(b) lifting up the cured resin layer for one layer formed in the step (a), thereby allowing the liquid dental photocurable resin composition to flow into the space between the lower face of the cured resin layer and the bottom face of the shaping container, and irradiating the dental photocurable resin composition between the lower face of the cured resin layer and the bottom face of the shaping container with light in a predetermined shape pattern through the light permeable bottom face of the shaping container in accordance with slice data every one layer based on three-dimensional CAD data relating to a tooth to further form a cured resin layer having a predetermined shape pattern for one layer, and
(c) repeating the operation of the step (b) until the objective artificial tooth is obtained.

Stereolithography, in which a liquid photocurable resin composition is accommodated in a shaping container having a light permeable bottom face and light is irradiated from the bottom of the container to produce a stereoscopically shaped article, is called a regulated liquid surface stereolithography, and it has already been known (see Patent documents 6 and 7).

However, there has never been produced an artificial tooth using a regulated liquid surface stereolithography. Under these circumstances, it has never been known that, when an artificial tooth is produced by a regulated liquid surface stereolithography using a photocurable resin composition not having high photocuring sensitivity such as "liquid dental photocurable resin composition containing a radical polymerizable organic compound (A), a filler (B), and a photosensitive radical polymerization initiator (C)", it is possible to produce an artificial tooth which is excellent in aesthetic property, hardness, strength, functionality, fitness, and the like in a short optical shaping time of less than 1 hour, simply and smoothly, and the present inventors have first found this fact. In the case of performing a method for producing an artificial tooth, in which a liquid dental photocurable resin composition containing a radical polymerizable organic compound (A), a filler (B), and a photosensitive radical polymerization initiator (C) is accommodated in a shaping container and then the upper surface of the dental photocurable resin composition is irradiated with light in accordance with an optical shaping method which has most widely been employed, heretofore, without using the method of the present invention, it is impossible to produce an artificial tooth in a short time of less than 1 hour. From such point of view, the above-mentioned effects of the present invention exerted by producing an artificial tooth by employing a regulated liquid surface stereolithography are something utterly unexpected.

It is not clear why an artificial tooth which is excellent in aesthetic property, hardness, strength, functionality, fitness, and the like, can be produced in a significantly short optical shaping time when an artificial tooth is produced by a regulated liquid surface stereolithography using a liquid dental photocurable resin composition containing a radical polymerizable organic compound (A), a filler (B), and a photosensitive radical polymerization initiator (C). However, it is estimated that the liquid dental photocurable resin composition flowed into the regulated space between the lower face of the cured resin layer and the bottom face of the shaping container is cured by light irradiated through the bottom face without being exposed to air, and thus curing inhibition due to oxygen does not occur and photocuring is performed quickly and surely.

In the shaping container accommodating a liquid dental photocurable resin composition, the entire bottom face may be formed of a light permeability material, or the periphery of the bottom face may be formed of a material which does not transmit light, and also the portion (center portion) surrounded by the periphery may be formed of a light permeable material, and thus making it possible to decide the area of the light permeable portion in the bottom face according to the maximum size of the artificial tooth produced by each shaping container, corresponding maximum area of light to be irradiated through the bottom face of the shaping container, and the like.

It is possible to use, as the material which forms the light permeable bottom face of the shaping container, transparent glass, transparent plastic, and the like.

Ultraviolet ray and visible light, each having a wavelength of 300 to 450 nm, are used as light which is irradiated through the light permeable bottom face of the shaping container. It is possible to use, as the light source, laser beam (for example, semiconductor excitation solid laser capable of emitting ultraviolet light, Ar laser, He—Cd laser, ultraviolet LED laser (light-emitting diode), LED laser capable of emitting light having a wavelength of 380 to 450 nm), a high-pressure mercury lamp, an ultrahigh-pressure air gun mercury lamp, a low-pressure mercury lamp, a xenon lamp, a halogen lamp, a metal halide lamp, an ultraviolet LED lamp, an ultraviolet fluorescent lamp, and the like. Of these light sources, a LED laser or LED lamp capable of emitting light having a wavelength of about 400 nm (usually about 380 to 410 nm) is particularly preferably used in view of handiness of a device, economy, maintainability, and the like.

In a conventionally used method in which a stereoscopically shaped article is produced by irradiating a photocurable resin composition accommodated in a shaping container with light from the upper surface, optical shaping is usually performed by irradiating with ultraviolet laser beam having a wavelength of 300 to 370 nm, and a light source for emitting ultraviolet laser beam having a wavelength of 300 to 370 nm is generally expensive.

To the contrary, according to the present invention, as mentioned above, it is possible to smoothly produce an artificial tooth which is excellent in aesthetic property, hardness, strength, functionality, fitness, and the like in a short time even by irradiation with light which has lower energy intensity than that of the above ultraviolet laser beam and also has a wavelength of 380 to 450 nm (light in a visible range), and a light source for emitting light having a wavelength of 380 to 450 nm (light in a visible range) is inexpensive and easily available as compared with the light source for emitting ultraviolet laser beam having a wavelength of 300 to 370 nm.

In the case of forming each cured resin layer by irradiating a liquid dental photocurable resin composition accommodated in a shaping container with light through the light permeable bottom face of the shaping container, it is possible to employ a method in which a cured resin layer is formed by irradiating a dental photocurable resin composition with light converted to a spot shape, such as laser beam, through the light permeable bottom face of the shaping container using a line drawing method, or a method in which a cured resin layer is formed by planar irradiation of a dental photocurable resin composition with light passed through a planar drawing mask formed by arranging a plurality of micro-optical shutters such as a liquid crystal shutter or a digital micromirror device (DMD) through the light permeable bottom face of the shaping container.

According to the method of the present invention, it is possible to produce an artificial tooth used as a provisional tooth for only a short time until a final tooth is mounted (provisional tooth for post crown, provisional tooth for partial false teeth, provisional tooth full set of false teeth), an artificial tooth used as a final tooth (final tooth for post crown, final tooth for partial false teeth, final tooth for full set of false teeth), a denture for training of dental student, and the like in a short time, simply and smoothly.

EXAMPLES

The present invention will be specifically described below by way of Examples, but the present invention is not limited to the following Examples.

Example 1

(1) Urethane dimethacrylate ("U-2TH", manufactured by Shin Nakamura Chemical Co., Ltd.) (48 g) obtained by the reaction of 1 mol of 2,2,4-trimethylhexamethylene diisocyanate with 2 mol of 2-hydroxyethyl methacrylate, which is represented by the formula "$CH_2=C(CH_3)-CO-O-CH_2CH_2-O-CO-NH-[CH_2C(CH_3)_2CH_2CH(CH_3)CH_2CH_2]-NH-CO-O-CH_2CH_2-O-C0-(CH_3)C=CH_2$", 12 g of triethylene glycol dimethacrylate ("NK-3G", manufactured by Shin Nakamura Chemical Co., Ltd.), and 0.6 g of 2,4,6-trimethylbenzoyl-diphenyl-phosphine oxide ("Lucirin TPO", photosensitive radical polymerization initiator, manufactured by BASF Corporation) were mixed, followed by stirring to prepare a photocurable resin, and then the mixture was mixed with 33.6 g of a methacrylsilane-treated silica powder ("Admafine SO-C1", average particle diameter of 0.25 μm, manufactured by Admatechs Company Limited) to prepare a liquid dental photocurable resin composition.

Using a B type viscometer ("DV-E", manufactured by Brookfield Engineering Laboratories, Inc.), the viscosity of the thus obtained dental photocurable resin composition was measured at 25° C. As a result, it was 1,360 mPa·s.

(2) Using the dental photocurable resin composition obtained in the above (1), optical shaping was performed by a regulation level optical shaping device of a type in which light is irradiated from the bottom side through the light permeable bottom face of a shaping container using a line drawing system ("DigitalWax 029D", manufactured by DWS SRL) under the conditions of a laser output of 30 mW, a wavelength of 405 nm, a beam diameter of 0.02 mm, a laser operation rate of 4,600 mm/sec, and a one layer thickness of 0.05 mm in accordance with slice data every one layer based on three-dimensional CAD data relating to a tooth to produce an artificial tooth for four true teeth (height of 13.1 mm) shown in the photograph of FIG. 1 over 40 minutes (the photograph of FIG. 1 is displayed in the same state as in the case of shaping).

Figure 2:
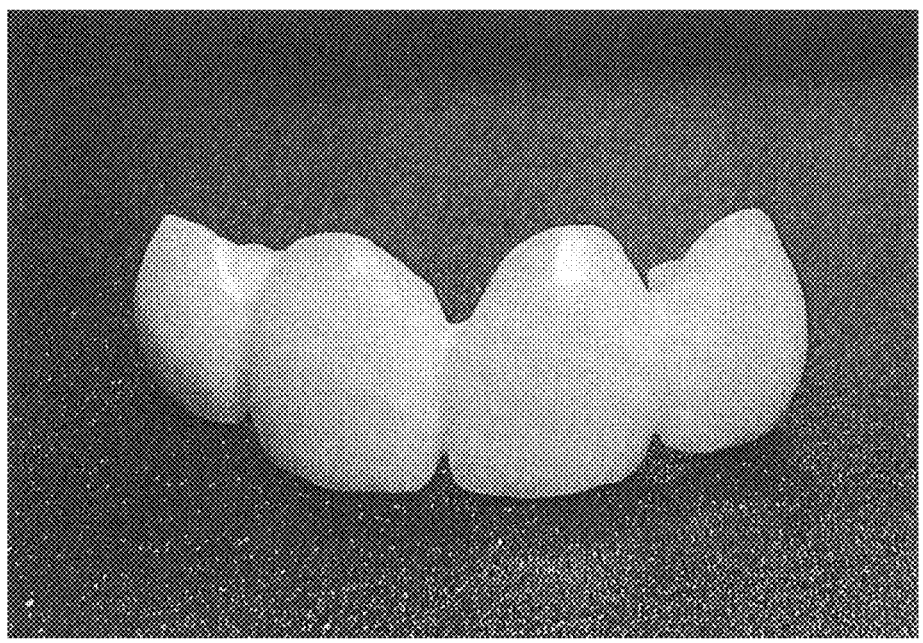
FIG. 2 is a photograph taking provisional teeth which are obtained by cutting off a supporting member from provisional teeth including a supporting member obtained in Example 1, washing with an alcohol, grinding a surface, and polishing the surface.

(3) After removing a supporting member from the artificial tooth obtained in the above (2) and washing with ethanol, and further post exposing for 20 minutes using a post exposure device (post exposure device "UV curing unit S2", manufactured by DWS SRL), a surface was simply ground and polished to produce an artificial tooth shown in the photograph of FIG. 2 (photograph of FIG. 2 is displayed in a vertically inverted state as compared with FIG. 1), and this artificial tooth was used for the patient as a true tooth.

(4) Using the liquid dental photocurable resin composition obtained in the above (1), dumbbells and bars for the measurement of tensile property and bending property were produced by the regulation level optical shaping device (DigitalWax 029D) used in the above (2) under the same conditions as in the above (2) in accordance with JIS K6251, and then tensile property and bending property were measured in accordance with JIS K6251 using a measuring device manufactured by Shimadzu Corporation (AutoGraph AG-XPlus).

Using ASKER, Model D, manufactured by KOBUNSHI KEIKI CO., LTD., surface hardness was measured as Shore D hardness, while water absorption was measured in accordance with JIS 7209 (ISO 62).

The results are shown in Table 1 below.

As is apparent from Table 1, the stereoscopically shaped article obtained in (4) exhibits practically sufficient physical properties (mechanical strength represented by surface hardness and bending strength) and sufficiently low water absorption.

Example 2

(1) Urethane dimethacrylate ("U-2TH", manufactured by Shin Nakamura Chemical Co., Ltd.) (48 g) obtained by the reaction of 1 mol of 2,2,4-trimethylhexamethylene diisocyanate with 2 mol of 2-hydroxyethyl methacrylate, which is represented by the formula "$CH_2=C(CH_3)-CO-O-CH_2CH_2-O-CO-NH-[CH_2C(CH_3)_2CH_2CH(CH_3)CH_2CH_2]-NH-CO-O-CH_2CH_2-O-C0-(CH_3)C=CH_2$", 12 g of triethylene glycol dimethacrylate ("NK-3G", manufactured by Shin Nakamura Chemical Co., Ltd.), and 0.6 g of 2,4,6-trimethylbenzoyl-diphenyl-phosphine oxide ("Lucirin TPO", photosensitive radical polymerization initiator, manufactured by BASF Corporation) and 0.001 g of a colorant ("Macrolex Orange 3G", manufactured by LANXESS Corp) were mixed, followed by stirring to prepare a photocurable resin, and then the mixture was mixed with 33.6 g of a methacrylsilane-treated silica powder ("Admafine SO-C1", average particle diameter of 0.25 μm, manufactured by Admatechs Company Limited) and 9.4 g of a spherical glass powder ("Spheriglass 7010", manufactured by Potters Industries Inc.) to prepare a liquid dental photocurable resin composition.

Using a B type viscometer ("DV-E", manufactured by Brookfield Engineering Laboratories, Inc.), the viscosity of the thus obtained dental photocurable resin composition was measured at 25° C. As a result, it was 1,400 mPa·s.

(2) Using the liquid dental photocurable resin composition obtained in the above (1), optical shaping was performed by the same regulation level optical shaping device used in Example 1(2) under the same conditions as in Example 1(2) to produce an artificial tooth for three true teeth (height of 13.1 mm) shown in the photograph of FIG. 1 over 35 minutes.

(3) After removing a supporting member from the artificial tooth obtained in the above (2) and washing with ethanol, and further post exposing for 20 minutes using the same post exposure device used in Example 1(3), a surface was simply ground and polished to produce an artificial tooth having A1-class color tone, and this artificial tooth was used for the patient as a true tooth.

(4) Using the liquid dental photocurable resin composition obtained in the above (1), a stereoscopically shaped article was produced in the same manner as in Example 1(4), and then various physical properties were produced in the same manner as in Example 1(4) to obtain the results as shown in the following Table 1.

Example 3

(1) Urethane dimethacrylate ("U-2TH", manufactured by Shin Nakamura Chemical Co., Ltd.) (48 g) obtained by the reaction of 1 mol of 2,2,4-trimethylhexamethylene diisocyanate with 2 mol of 2-hydroxyethyl methacrylate, which is represented by the formula "$CH_2=C(CH_3)-CO-O-CH_2CH_2-O-CO-NH-[CH_2C(CH_3)_2CH_2CH(CH_3)CH_2CH_2]-NH-CO-O-CH_2CH_2-O-C0-(CH_3)C=CH_2$", 12 g of triethylene glycol dimethacrylate ("NK-3G", manufactured by Shin Nakamura Chemical Co., Ltd.), and 0.6 g of 2,4,6-trimethylbenzoyl-diphenyl-phosphine oxide ("Lucirin TPO", photosensitive radical polymerization initiator, manufactured by BASF Corporation) were mixed, followed by stirring to prepare a photocurable resin, and then the mixture was mixed with 22.4 g of a methacrylsilane-treated silica powder ("Admafine SO-C1", average particle diameter of 0.25 μm, manufactured by Admatechs Company Limited) and 11.2 g of a methacrylsilane-treated alumina powder ("Admafine AO-502", average particle diameter 0.7 μm, manufactured by Admatechs Company Limited) to prepare a liquid dental photocurable resin composition.

Using a B type viscometer ("DV-E", manufactured by Brookfield Engineering Laboratories, Inc.), the viscosity of the thus obtained dental photocurable resin composition was measured at 25° C. As a result, it was 1,400 mPa·s.

(2) Using the liquid dental photocurable resin composition obtained in the above (1), optical shaping was performed by the same regulation level optical shaping device used in Example 1(2) under the same conditions as in Example 1(2) to produce an artificial tooth for three true teeth (height of 13.1 mm) shown in the photograph of FIG. 1 over 35 minutes.

(3) After removing a supporting member from the artificial tooth obtained in the above (2) and washing with ethanol, and further post exposing for 20 minutes using the same post exposure device used in Example 1(3), a surface was simply ground and polished to produce an artificial tooth, and this artificial tooth was used for the patient as a true tooth.

(4) Using the liquid dental photocurable resin composition obtained in the above (1), a stereoscopically shaped article was produced in the same manner as in Example 1(4), and then various physical properties were produced in the same manner as in Example 1(4) to obtain the results as shown in the following Table 1.

Comparative Example 1

(1) The same operation as in Example 1(1) was performed to prepare the same liquid dental photocurable resin composition as in Example 1(1).

(2) An attempt was made to produce an artificial tooth for four true teeth (height of 13.1 mm) by accommodating the dental photocurable resin composition obtained in the above (1) in a shaping container of an stereolithography device of a system in which light is irradiated from upper surface of the photocurable resin composition ("RM-3000", manufactured by CMET Inc.) and performing optical shaping under the conditions of a laser output of 200 mW, a wavelength of 355 nm, a beam diameter of 0.2 mm, a laser operation rate of 3,000 mm/sec, and a one layer thickness of 0.05 mm in accordance with slice data every one layer based on three-dimensional CAD data relating to a tooth. However, in this device using a free liquid level method, since photocuring liquid level is always in contact with oxygen (air), curing inhibition due to oxygen occurred and thus curing of the photocurable resin composition was not sufficiently performed. Although shaping could be performed, the surface is uncured and "sticky", thus failing to product a practical artificial tooth.

TABLE 1

| | Example 1 | Example 2 | Example 3 | Comparative Example 1 |
|---|---|---|---|---|
| Viscosity of dental photocurable resin composition (mPa·s) (25° C.) | 1,360 | 1,400 | 1,400 | 1,360 |
| Tensile strength (MPa) | 42 | 44 | 42 | —[1)] |
| Tensile modulus (MPa) | 2,400 | 2,700 | 2,500 | —[1)] |
| Flexural strength (MPa) | 87 | 89 | 86 | —[1)] |
| Flexural modulus (MPa) | 2,700 | 2,800 | 2,700 | —[1)] |
| Surface hardness (Shore D) | 92 | 92 | 92 | —[1)] |
| Water absorption % (23° C./24 hours) | 0.15% | 0.16% | 0.16% | —[1)] |
| Appearance | Good | Good | Good | —[1)] |

[1)]not measured because of uncured surface.

As is apparent from the results shown in Table 1, artificial teeth obtained in Examples 1 to 3 can be effectively used as an artificial tooth (true tooth) since they have satisfactory surface hardness, tensile strength, tensile elastic modulus, bending strength, and bending elastic modulus and also exhibit low water absorption.

To the contrary, as is apparent from the results of Comparative Example 1, even when using a dental photocurable resin composition with the same composition as that of Example 1, a practical artificial tooth could not be produced in a short optical shaping time when an artificial tooth is produced by irradiating the upper surface of a dental photocurable resin composition with light in accordance with an optical shaping method which has most widely been employed, heretofore.

Example 4

(1) 2,2-Bis[4-(3-(meth)acryloyloxy)-2-hydroxypropoxyphenyl]propane ("EMA-100", manufactured by Shin Nakamura Chemical Co., Ltd.) (40 g), 27 g of triethylene glycol dimethacrylate ("NK-3G", manufactured by Shin Nakamura Chemical Co., Ltd.), and 0.6 g of 2,4,6-trimethylbenzoyl-diphenyl-phosphine oxide ("Lucirin TPO", photosensitive radical polymerization initiator, manufactured by BASF Corporation) were mixed, followed by stirring to prepare a photocurable resin, and then the mixture was mixed with 33 g of a methacrylsilane-treated silica powder ("Admafine SO-C1", average particle diameter of 0.25 μm, manufactured by Admatechs Company Limited) to prepare a liquid dental photocurable resin composition.

Using a B type viscometer ("DV-E", manufactured by Brookfield Engineering Laboratories, Inc.), the viscosity of the thus obtained dental photocurable resin composition was measured at 25° C. As a result, it was 1,460 mPa·s.

(2) Using the liquid dental photocurable resin composition obtained in the above (1), optical shaping was performed by the same regulation level optical shaping device used in Example 1(2) under the same conditions as in Example 1(2) to produce an artificial tooth for four provisional teeth (height of 13.1 mm) over 40 minutes.

(3) After removing a supporting member from the artificial tooth obtained in the above (2) and washing with ethanol, and further post exposing for 20 minutes using the same post exposure device used in Example 1(3), a surface was simply ground and polished to produce an artificial tooth, and this artificial tooth was used for the patient as a provisional tooth.

Example 5

(1) 2,2-Bis[4-(3-(meth)acryloyloxy)-2-hydroxypropoxyphenyl]propane ("EMA-100", manufactured by Shin Nakamura Chemical Co., Ltd.) (60 g), 40 g of triethylene glycol dimethacrylate ("NK-3G", manufactured by Shin Nakamura Chemical Co., Ltd.), and 1.0 g of 2,4,6-trimethylbenzoyl-diphenyl-phosphine oxide ("Lucirin TPO", photosensitive radical polymerization initiator, manufactured by BASF Corporation) were mixed, followed by stirring to prepare a photocurable resin, and then the mixture was mixed with 30 g of a methacrylsilane-treated silica powder ("Admafine SO-C1", average particle diameter of 0.25 μm, manufactured by Admatechs Company Limited) and 5 g of a methacrylsilane-treated alumina powder ("Admafine AO-502", average particle diameter 0.7 μm, manufactured by Admatechs Company Limited) to prepare a liquid dental photocurable resin composition.

Using a B type viscometer ("DV-E", manufactured by Brookfield Engineering Laboratories, Inc.), the viscosity of the thus obtained dental photocurable resin composition was measured at 25° C. As a result, it was 1,460 mPa·s.

(2) Using the liquid dental photocurable resin composition obtained in the above (1), optical shaping was performed by the same regulation level optical shaping device used in Example 1(2) under the same conditions as in Example 1(2) to produce an artificial tooth for four provisional teeth (height of 13.1 mm) over 40 minutes.

(3) After removing a supporting member from the artificial tooth obtained in the above (2) and washing with ethanol, and further post exposing for 20 minutes using the same post exposure device used in Example 1(3), a surface was simply ground and polished to produce an artificial tooth, and this artificial tooth was used for the patient as a provisional tooth.

Example 6

(1) 2,2-Bis[4-(3-(meth)acryloyloxy)-2-hydroxypropoxyphenyl]propane ("EMA-100", manufactured by Shin Nakamura Chemical Co., Ltd.) (40 g), 27 g of triethylene glycol dimethacrylate ("NK-3G", manufactured by Shin Nakamura Chemical Co., Ltd.), and 0.6 g of 2,4,6-trimethylbenzoyl-diphenyl-phosphine oxide ("Lucirin TPO", photosensitive radical polymerization initiator, manufactured by BASF Corporation) were mixed, followed by stirring to prepare a photocurable resin, and then the mixture was mixed with 33 g of a methacrylsilane-treated silica powder ("Admafine SO-C1", average particle diameter of 0.25 μm, manufactured by Admatechs Company Limited) to prepare a liquid dental photocurable resin composition.

Using a B type viscometer ("DV-E", manufactured by Brookfield Engineering Laboratories, Inc.), the viscosity of the thus obtained dental photocurable resin composition was measured at 25° C. As a result, it was 1,460 mPa·s.

(2) Using the liquid dental photocurable resin composition obtained in the above (1), optical shaping was performed by a regulation level optical shaping device ("DigitalWax 009J", manufactured by DWS SRL) of a DMD type in which light from a LED lamp is planarly irradiated from the bottom side through the light permeable bottom face of a shaping container under the conditions of a wavelength of 405 nm, a one layer thickness of 0.05 mm, and a one layer light irradiation time of 7 seconds in accordance with slice data every one layer based on three-dimensional CAD data relating to a tooth to produce an artificial tooth for four provisional teeth (height of 13.1 mm) over 40 minutes.

(3) After removing a supporting member from the artificial tooth obtained in the above (2) and washing with ethanol, and further post exposing for 20 minutes using the same post exposure device used in Example 1(3), a surface was simply ground and polished to produce an artificial tooth, and this artificial tooth was used for the patient as a provisional tooth.

INDUSTRIAL APPLICABILITY

According to a method of the present invention for producing an artificial tooth, it is possible to produce an artificial tooth which is excellent in aesthetic property, hardness, strength, functionality, fitness, and the like in a short time, simply and smoothly, without requiring skill.

The invention claimed is:
1. A method for producing an artificial true tooth, which comprises the steps of:
   (a) accommodating a liquid dental photocurable resin composition containing a radical polymerizable organic compound (A), a filler (B), and a photosensitive radical polymerization initiator (C) in a shaping container having a bottom face, and irradiating the dental photocurable resin composition in the shaping container in a predetermined shape pattern through the bottom face of the shaping container in accordance with slice data every one layer based on three-dimensional CAD data relating to a tooth to form a cured resin layer having the predetermined shape pattern for one layer;
   (b) lifting up the cured resin layer for one layer formed in the step (a), thereby allowing the liquid dental photocurable resin composition to flow between the lower face of the cured resin layer and the bottom face of the shaping container, and irradiating the dental photocurable resin composition between the lower face of the cured resin layer and the bottom face of the shaping container through the bottom face of the shaping container in accordance with slice data every one layer based on three-dimensional CAD data relating to a tooth to further form a cured resin layer having the predetermined shape pattern for one layer, and
   (c) repeating the operation of the step (b) until the objective artificial true tooth is obtained;
   wherein the filler (B) has an average particle diameter between 0.01 to 10 μm and is selected from the group consisting of: a silica powder, an alumina powder, a zirconia powder, and a glass powder, wherein the above powders are prepared by treating the above powders with a coupling agent; and
   wherein the liquid dental photocurable resin composition contains, as the radical polymerizable organic compound (A), a urethane-based di(meth)acrylate compound (A-1a) obtained by the reaction of 1 mol of an organic diisocyanate compound with 2 mol of hydroxyalkyl (meth)acrylate, represented by the following general formula (A-1a):

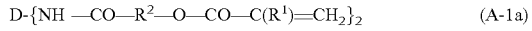

wherein $R^1$ represents a methyl group, $R^2$ represents an alkylene group, and D represents an organic diisocyanate compound residue, and a di(meth)acrylate compound (A-1b) obtained by the reaction of 1 mol of a diepoxy compound with 2 mol of (meth)acrylic acid, represented by the following general formula (A-1b):

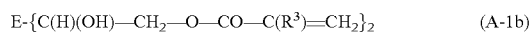

wherein $R^3$ represents a methyl group, and E represents a diepoxy compound residue wherein the organic diisocyanate compound is composed of at least one aliphatic diisocyanate compound, selected from the group consisting of: hexamethylene diisocyanate, 2,2,4-trimethylhexamethylene diisocyanate, isophorone diisocyanate, hydrogenated diphenylmethane diisocyanate, hydrogenated m-xylylene diisocyanate, and hydrogenated toluene diisocyanate; and at least one aromatic diisocyanate selected from the group consisting of: diphenylmethane diisocyanate, toluene diisocyanate, and xylylene diisocyanate; and wherein the hydroxyalkyl (meth) acrylate is selected from the group consisting of: hydroxyethyl (meth)acrylate, hydroxypropyl (meth)acrylate, hydroxybutyl (meth)acrylate, hydroxypentyl (meth)acrylate, and hydroxyhexyl (meth)acrylate and wherein the method the artificial true tooth in less than an hour.

2. The method for producing an artificial tooth according to claim 1, wherein three-dimensional CAD data relating to a tooth are data obtained using a computed tomography device (CT device), a magnetic resonance imaging device (MRI), a computed radiographic device (CR device), or an intraoral 3D scanner.

3. The method for producing an artificial tooth according to claim 1, wherein, in the liquid dental photocurable resin composition, the content of the radical polymerizable organic compound (A) is 30 to 95% by mass based on the total mass of the dental photocurable resin composition, the content of filler (B) is 5 to 70% by mass based on the total mass of the dental photocurable resin composition, and the content of the photosensitive radical polymerization initiator (C) is 0.01 to 5% by mass based on the mass of the radical polymerizable organic compound (A).

4. The method for producing an artificial tooth according to claim 1, wherein the content of at least one of the urethane-based di(meth)acrylate compound (A-1a) and the di(meth)acrylate compound (A-1b) is 5 to 95% by mass based on the mass of the radical polymerizable organic compound (A).

5. The method for producing an artificial tooth according to claim 4, wherein the liquid dental photocurable resin composition comprises, in place of the radical polymerizable organic compound (A), another radical polymerizable organic compound (A-2), together with at least one of the urethane-based di(meth)acrylate compound (A-1a) and the di(meth)acrylate compound (A-1b).

6. The method for producing an artificial tooth according to claim 4, wherein the content of another radical polymerizable organic compound (A-2) is 5 to 70% by mass based on the mass of the radical polymerizable organic compound (A).

7. The method for producing an artificial tooth according to claim 1, wherein a liquid dental photocurable resin composition is irradiated with light converted to a spot shape by linearly moving through the bottom face of the shaping container to form a cured resin layer, or a liquid dental photocurable resin composition is irradiated planarly with light passed formed by arranging a plurality of micro-optical shutters through the bottom face of the shaping container.

8. A method for producing an artificial true tooth, which comprises the steps of:
(a) accommodating a liquid dental photocurable resin composition containing a radical polymerizable organic compound (A), a filler (B), and a photosensitive radical polymerization initiator (C) in a shaping container having a bottom face, and irradiating the dental photocurable resin composition in the shaping container in a predetermined shape pattern through the bottom face of the shaping container in accordance with slice data every one layer based on three-dimensional CAD data relating to a tooth to form a cured resin layer having the predetermined shape pattern for one layer;
(b) lifting up the cured resin layer for one layer formed in the step (a), thereby allowing the liquid dental photocurable resin composition to flow between the lower face of the cured resin layer and the bottom face of the shaping container, and irradiating the dental photocurable resin composition between the lower face of the cured resin layer and the bottom face of the shaping container through the bottom face of the shaping container in accordance with slice data every one layer based on three-dimensional CAD data relating to a tooth to further form a cured resin layer having the predetermined shape pattern for one layer, and
(c) repeating the operation of the step (b) until the objective artificial tooth is obtained;
wherein the filler (B) has an average particle diameter between 0.01 to 10 μm and is selected from the group consisting of: a silica powder, an alumina powder, a zirconia powder, and a glass powder, wherein the above powders are prepared by treating the above powders with a coupling agent; and
wherein the liquid dental photocurable resin composition contains, as the radical polymerizable organic compound (A), a urethane-based di(meth)acrylate compound (A-1a) obtained by the reaction of 1 mol of an organic diisocyanate compound with 2 mol of hydroxyalkyl (meth)acrylate, represented by the following general formula (A-1a):

$$D\text{-}\{NH\text{—}CO\text{—}O\text{—}R^2\text{—}O\text{—}CO\text{—}C(R^1)\text{=}CH_2\}_2 \quad (A\text{-}1a)$$

wherein $R^1$ represents a methyl group, $R^2$ represents an alkylene group, and D represents an organic diisocyanate compound residue,
and a di(meth)acrylate compound (A-1b) obtained by the reaction of 1 mol of a diepoxy compound with 2 mol of (meth)acrylic acid, represented by the following general formula (A-1b):

$$E\text{-}\{C(H)(OH)\text{—}CH_2\text{—}O\text{—}CO\text{—}C(R^3)\text{=}CH_2\}_2 \quad (A\text{-}1b)$$

wherein $R^3$ represents a methyl group, and E represents a diepoxy compound residue, and
a content of at least one of the urethane-based di(meth)acrylate compound (A-1a) and the di(meth)acrylate compound (A-1b) is 5 to 95% by mass based on the mass of the radical polymerizable organic compound (A) and
the liquid dental photocurable resin composition also contains, as another radical polymerizable organic compound (A-2), oligo ethylene glycol di(meth)acrylate; and wherein the method produces the artificial true tooth in less than an hour.

9. A method for producing an artificial true tooth, which comprises the steps of:
(a) accommodating a liquid dental photocurable resin composition, containing a radical polymerizable organic compound (A), a filler (B), and a photosensitive radical polymerization initiator (C) in a shaping container having a bottom face, and irradiating the dental photocurable resin composition in the shaping container in a predetermined shape pattern through the bottom face of the shaping container in accordance with slice data every one layer based on three- dimensional CAD data relating to a tooth to form a cured resin layer having the predetermined shape pattern for one layer;
(b) lifting up the cured resin layer for one layer formed in the step (a), thereby allowing the liquid dental photocurable resin composition to flow between the lower face of the cured resin layer and the bottom face of the shaping container, and irradiating the dental photocurable resin composition between the lower face of the cured resin layer and the bottom face of the shaping container through the bottom face of the shaping container in accordance with slice data every one layer based on three-dimensional CAD data relating to a tooth to further form a cured resin layer having the predetermined shape pattern for one layer, and
(c) repeating the operation of the step (b) until the objective artificial tooth is obtained;
wherein the filler (B) has an average particle diameter between 0.01 to 10 μm and is selected from the group consisting of: a silica powder, an alumina powder, a zirconia powder, and a glass powder, wherein the above powders are prepared by treating the above powders with a coupling agent; and
wherein the liquid dental photocurable resin composition contains, as the radical polymerizable organic compound (A), a urethane-based di(meth)acrylate compound (A-1a) obtained by the reaction of 1 mol of an organic diisocyanate compound with 2 mol of hydroxyalkyl (meth)acrylate, represented by the following general formula (A-1a):

$$D\text{-}\{NH\text{—}CO\text{—}O\text{—}R^2\text{—}O\text{—}CO\text{—}C(R^1)\text{=}CH_2\}_2 \quad (A\text{-}1a)$$

wherein $R^1$ represents a methyl group, $R^2$ represents an alkylene group, and D represents an organic diisocyanate compound residue, and
a di(meth)acrylate compound (A-1b) obtained by the reaction of 1 mol of a diepoxy compound with 2 mol of (meth)acrylic acid, represented by the following general formula (A-1b):

$$E\text{-}\{C(H)(OH)\text{—}CH_2\text{—}O\text{—}CO\text{—}C(R^3)\text{=}CH_2\}_2 \quad (A\text{-}1b)$$

wherein $R^3$ represents a methyl group, and E represents a diepoxy compound residue wherein the organic diisocyanate compound is composed of at least one aliphatic diisocyanate compound, selected from the group consisting of: hexamethylene diisocyanate, 2,2,4-trimethylhexamethylene diisocyanate, isophorone diisocyanate, hydrogenated diphenylmethane diisocyanate, hydrogenated m-xylylene diisocyanate, and hydrogenated toluene diisocyanate; and at least one aromatic diisocyanate selected from the group consisting of: diphenylmethane diisocyanate, toluene diisocyanate, and xylylene diisocyanate; and wherein the hydroxyalkyl (meth) acrylate is selected from the group consisting of: hydroxyethyl (meth)acrylate, hydroxypropyl (meth)acrylate, hydroxybutyl (meth)acrylate, hydroxypentyl (meth)acrylate, and hydroxyhexyl (meth)acrylate, wherein the liquid dental photocurable resin composition has a viscosity measured at 25° C. of 10,000 mPa*s or less.

* * * * *

UNITED STATES PATENT AND TRADEMARK OFFICE
CERTIFICATE OF CORRECTION

PATENT NO. : 11,147,656 B2
APPLICATION NO. : 14/908215
DATED : October 19, 2021
INVENTOR(S) : Tsuneo Hagiwara and Satoshi Iketani It is certified that error appears in the above-identified patent and that said Letters Patent is hereby corrected as shown below:

In the Claims

In Claim 1, at Column 22, Line 23, insert the word --produces-- after the word "method" and before the word "the", therefor.

Signed and Sealed this
Fourth Day of January, 2022

Drew Hirshfeld
*Performing the Functions and Duties of the*
*Under Secretary of Commerce for Intellectual Property and*
*Director of the United States Patent and Trademark Office*